(12) United States Patent
Klentzman et al.

(10) Patent No.: US 11,499,894 B2
(45) Date of Patent: Nov. 15, 2022

(54) SAMPLE PRESSURE REDUCING SYSTEM

(71) Applicant: Welker, Inc., Sugar Land, TX (US)

(72) Inventors: James T. Klentzman, Richmond, TX (US); Josh H. Welker, Richmond, TX (US)

(73) Assignee: Welker, Inc., Sugar Land, TX (US)

( * ) Notice: Subject to any disclaimer, the term of this patent is extended or adjusted under 35 U.S.C. 154(b) by 118 days.

(21) Appl. No.: 16/935,294

(22) Filed: Jul. 22, 2020

(65) Prior Publication Data

US 2022/0026314 A1    Jan. 27, 2022

(51) Int. Cl.
*E21B 49/08* (2006.01)
*G01N 1/14* (2006.01)
*G01N 33/28* (2006.01)

(52) U.S. Cl.
CPC ............. *G01N 1/14* (2013.01); *E21B 49/086* (2013.01); *G01N 33/2823* (2013.01); *G01N 2001/1427* (2013.01)

(58) Field of Classification Search
CPC ................. G01N 1/14; G01N 33/2823; G01N 2001/1427; E21B 49/086

USPC ...... 73/152.23, 863.01, 863.84, 864, 864.34, 73/864.35, 864.62; 166/264; 175/59; 417/375–404; 137/565.17, 565.18, 137/565.19
See application file for complete search history.

(56) References Cited

U.S. PATENT DOCUMENTS 5,988,765 A * 11/1999 Yamaguchi ........... B60T 8/3235
303/22.6
2001/0004449 A1* 6/2001 Suzuki ..................... G01N 1/14
134/22.12

FOREIGN PATENT DOCUMENTS

| CN | 209387358 | * | 9/2019 |
| KR | 0173965 | * | 5/1999 |

* cited by examiner

*Primary Examiner* — Robert R Raevis
(74) *Attorney, Agent, or Firm* — Husch Blackwell LLP (57) ABSTRACT

A sample pressure reducing system is provided that integrates various pressure applications into a single system that provides the end user with a high-integrity sample without damaging equipment. The system facilitates sampling high-pressure product into a low-pressure container. The system fills and transfers product to reduce pressure automatically and repeatedly.

15 Claims, 7 Drawing Sheets

SAMPLE PRESSURE REDUCING SYSTEM

CROSS-REFERENCE TO RELATED APPLICATIONS

None.

FIELD OF THE INVENTION

The present invention relates to a system for reducing pressure so that a crude oil sample may be taken without requiring a dramatic and quick decrease in pressure that both damages equipment and potentially alters the sample.

BACKGROUND OF THE INVENTION

Sampling of crude oil is well known in the oil and gas industry. During the sampling process, sampling usually occurs first downstream of the wellhead, either onshore or offshore. In many cases, the sampling system encounters pressures 1,000 psi or greater during these early samplings. Pressures should be low to sample for certain qualities, including but not limited to brine, sediment, and water ("BS&W"). At later points, sampling may be carried out for other concerns.

In those locations where crude oil is presented at higher pressures, there is the occasional desire to maintain the sample at that higher pressure to analyze the high vapor pressure components. High pressure cylinders designed for that purpose are well-known in the art and are embodied by U.S. Pat. No. 6,422,737.

In other downstream applications, it is necessary to reduce the pressure on a sample from high pressure (e.g., 3,800 psi) to very low, or zero psi. Such a pressure-drop across the sampling equipment, when quickly carried out, can damage equipment. There is a need for a steady and controlled pressure reduction for the crude oil sampling system in order to get the oil to an appropriate pressure to analyze, for example, for BS&W.

Previously, such a reduction method was included a single-step pressure drop that was damaging to equipment. Alternatively, the sample was not obtained at a high pressure early in the process, and instead the sample was taken further down the process at a much lower pressure.

SUMMARY OF THE INVENTION

The current invention is a sample pressure reducing system. The design of the current invention aims to better preserve equipment than prior art mechanisms and methods for reducing pressure for a sample. The system samples high-pressure product into a low-pressure container. The system fills and transfers sample product to automatically and repeatedly reduce the sample's pressure.

The sample pressure reducing system includes a dual cavity cylinder, a pre-charge gas tank that applies a blanket pressure to the dual cavity cylinder, a low-level and high-level proximity switch, two two-way actuated valves that act as an input and an output to the cylinder, respectively, a dual coil four-way solenoid valve, a sample pump four-way solenoid valve, an actuation gas or hydraulic system, and a low-pressure sample container with a high-level switch. The various functions that those components carry out to procure a sample are set forth below in greater detail.

To fill high-pressure product into the system's dual cavity cylinder, the cylinder's upper cavity should be connected to a pre-charge gas tank that is pressurized relative to (slightly below or slightly above) pipeline pressure. This pre-charge pressure lowers the dual cavity cylinder piston to contact the low-level proximity switch. The low-level proximity switch energizes the dual coil four-way solenoid valve to open the inlet actuated two-way valve and close the outlet actuated two-way valve on the dual cavity cylinder. The low-level proximity switch also energizes the sample pump four-way solenoid valve and allows product from a sample pump to fill into the bottom cavity of the dual cavity cylinder.

To transfer high-pressure product into a low-pressure container, the product is filled to a predetermined (e.g., 30%, 50%, 80%) volume, at which point the dual cavity cylinder piston contacts the high-level proximity switch. The high-level proximity switch may then energize the dual coil four-way solenoid valve to actuate both the inlet and outlet of the dual-acting two-way valve connected to the bottom of the dual cavity cylinder. More specifically, the actuated two-way inlet valve closes to isolate the high-pressure sample product in the dual cavity cylinder, and the actuated two-way outlet valve opens to transfer the product into the low-pressure container.

At the same time (or very near to the same time), the sample pump stops because actuation gas pressure has been temporarily interrupted at the sample pump four-way solenoid valve. In a hydraulic actuation system, a pressure switch on the actuated line halts the sample pump. As the product is pushed out of the dual cavity cylinder to the low-pressure container by the pre-charge gas tank pressure, the cylinder piston lowers and subsequently contacts the low-level proximity switch. The low-level proximity switch energizes the dual coil solenoid four-way valve and the sample pump four-way solenoid valve to repeat the fill cycle.

When the low-pressure sample container reaches 80% (or other predetermined value) full and contacts its high-level switch, the system power is turned off, and operation is halted until the system is reset.

DETAILED DESCRIPTION OF THE INVENTION

Figure 1:
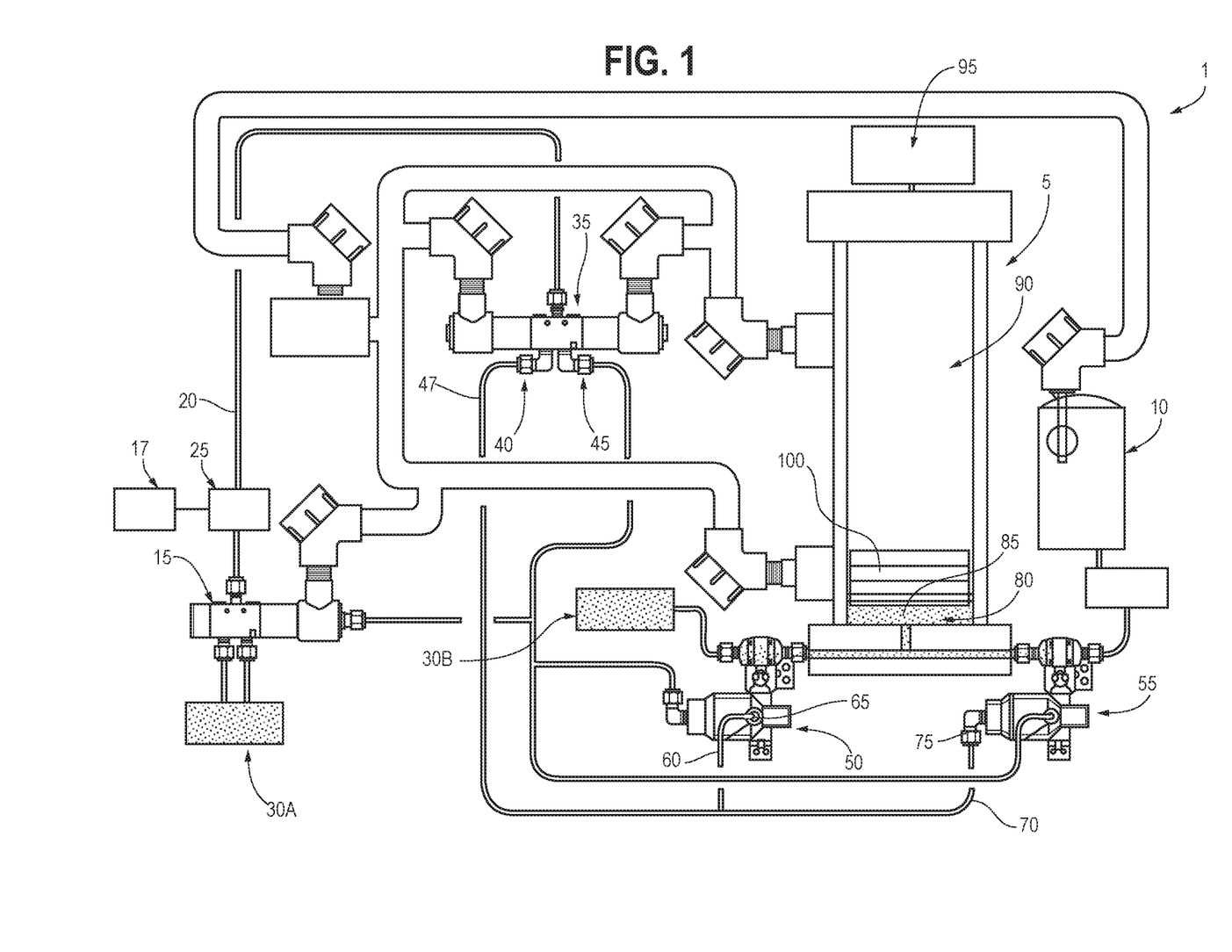
FIG. 1 is a first schematic of a pressure reducing system constructed according to the teachings of the present invention.

Referring to the drawings more particularly by reference numbers wherein like numbers refer to like parts, FIG. 1 illustrates a sample pressure reducing system 1, which hereinafter may be referred to in this application as the "system" 1. The system 1 draws a sample from a pipeline that is otherwise provided at a high pressure at a lower pressure to reduce the mechanical stress on its associated equipment.

The system 1 generally includes each of a dual cavity cylinder 5 in which a sample is temporarily contained, and a low-pressure sample container 10 to which that same sample is transferred. In operation, to transport a sample to the sample container 10, a sample pump four-way solenoid 15 may, when activated, introduce an actuation gas from an instrument air supply 17 to an air line 20 via an instrument regulator 25. This process may be initiated by an operator, or it may be pre-programmed and carried out by a digital controller, for example a programmable logic controller, or PLC (not illustrated).

When the solenoid 15 is activated, a sample may be drawn from a sampler 30A that air from the instrument regulator 25 may help to expel sample from the sampler 30A. The sampler is illustrated as each of 30A and 30B in two separate locations so that it can be described relative to each of the solenoid 15 and air line 20 that help to pump sample from the sampler 30A, and also relative to the valves (described below) that introduce sample from the sampler 30B to the dual-cavity cylinder 5 and the low-pressure sample container 10. The system 1 is preferably only in communication with one sampler, and the two samplers 30A and 30B are illustrated for explanatory purposes only.

While the solenoid 15 is activated, and when the cylinder 5 is under instruction to fill, a dual coil four-way solenoid 35 preferably is instructed (e.g., by the operator or PLC) to open a first valve 40 of the solenoid 35, while leaving a second valve 45 of the solenoid closed for the time being. When the first valve 40 is open, air may be provided along a first line 47 to each of a first two-way actuated valve 50 and a second two-way actuation valve 55. The valves 50, 55 are preferably ball valves that use the changing air flows to either open or close to allow sample to flow therethrough.

A first air input line 60 enters the first valve 50 at an input 65, but a second air input line 70 enters the second valve 55 at an output 75. As such, when the solenoid 35 has caused the valve 40 to open, air travels through the first valve 50 but is prevented from entering the second valve 55. Air entering the open valve 50 causes sample from the sampler 30B to be provided to the dual cavity cylinder 5 via the valve 50.

The dual cavity cylinder 5 includes each of a first cavity 80 in which high-pressure sample 85 is introduced and a second cavity 90 to which a blanket gas is applied, for example by a pre-charge gas tank 95 that is pressurized relative to pipeline pressure. The blanket gas may be, for example, Nitrogen. A piston 100 preferably separates the cavities 80, 90 from one another. As the sample 85 is introduced to the cavity 80, the pre-charge gas tank 95 applies the blanket pressure to the second cavity 90 and thus the piston 100.

Figure 2:
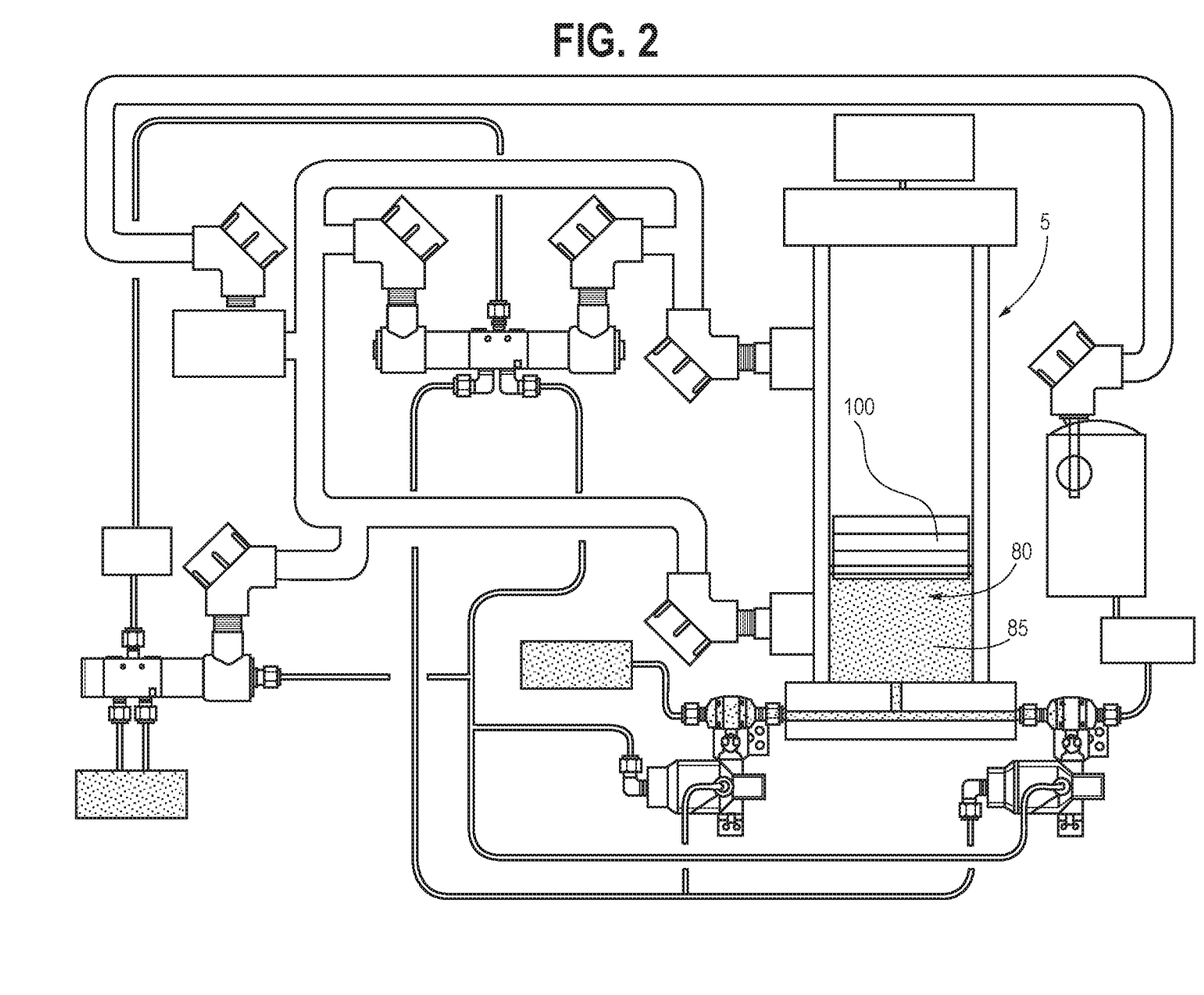
FIG. 2 is a second schematic of the pressure reducing system of FIG. 1.
Figure 3:
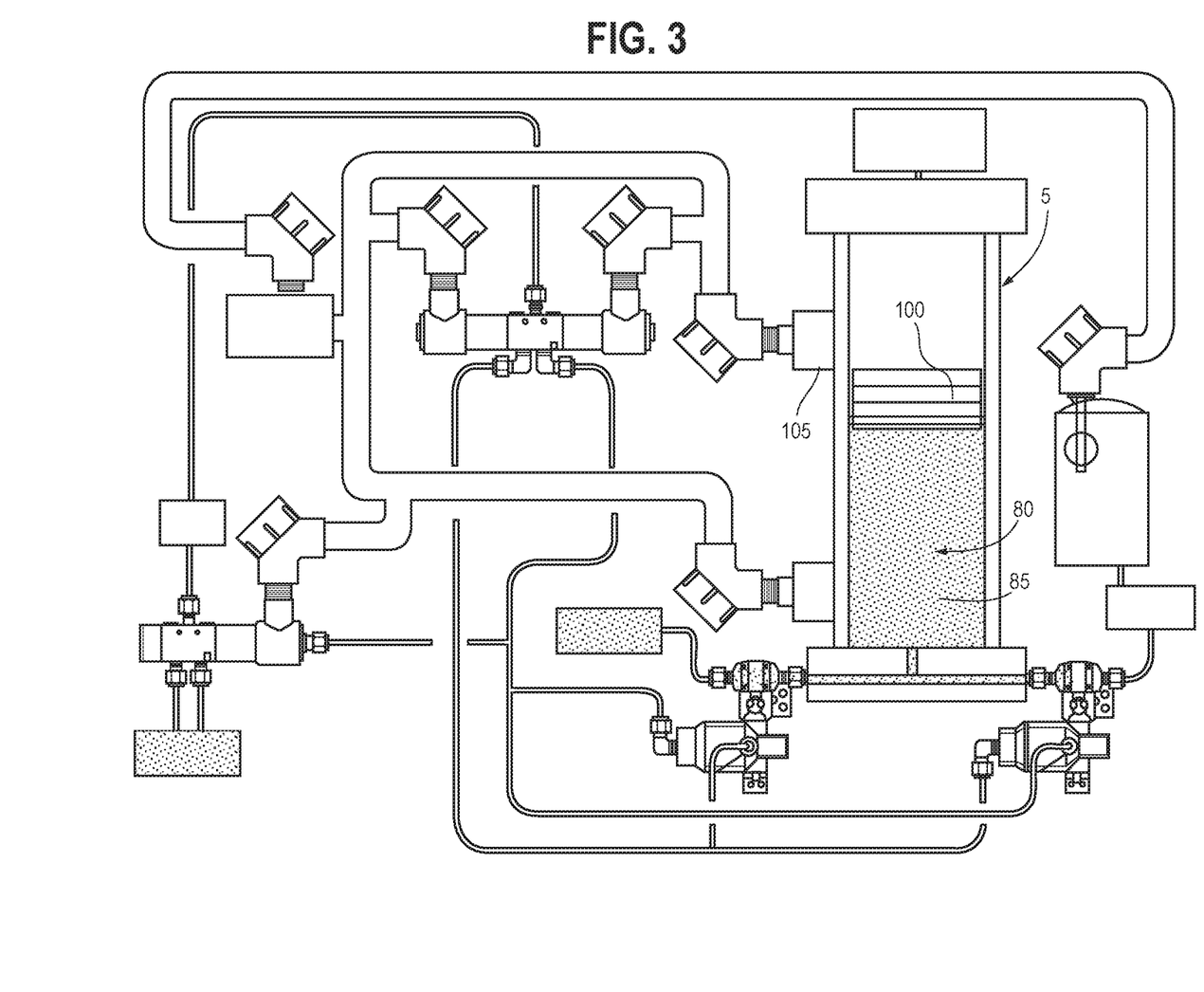
FIG. 3 is a third schematic of the pressure reducing system of FIGS. 1 and 2.
Figure 4:
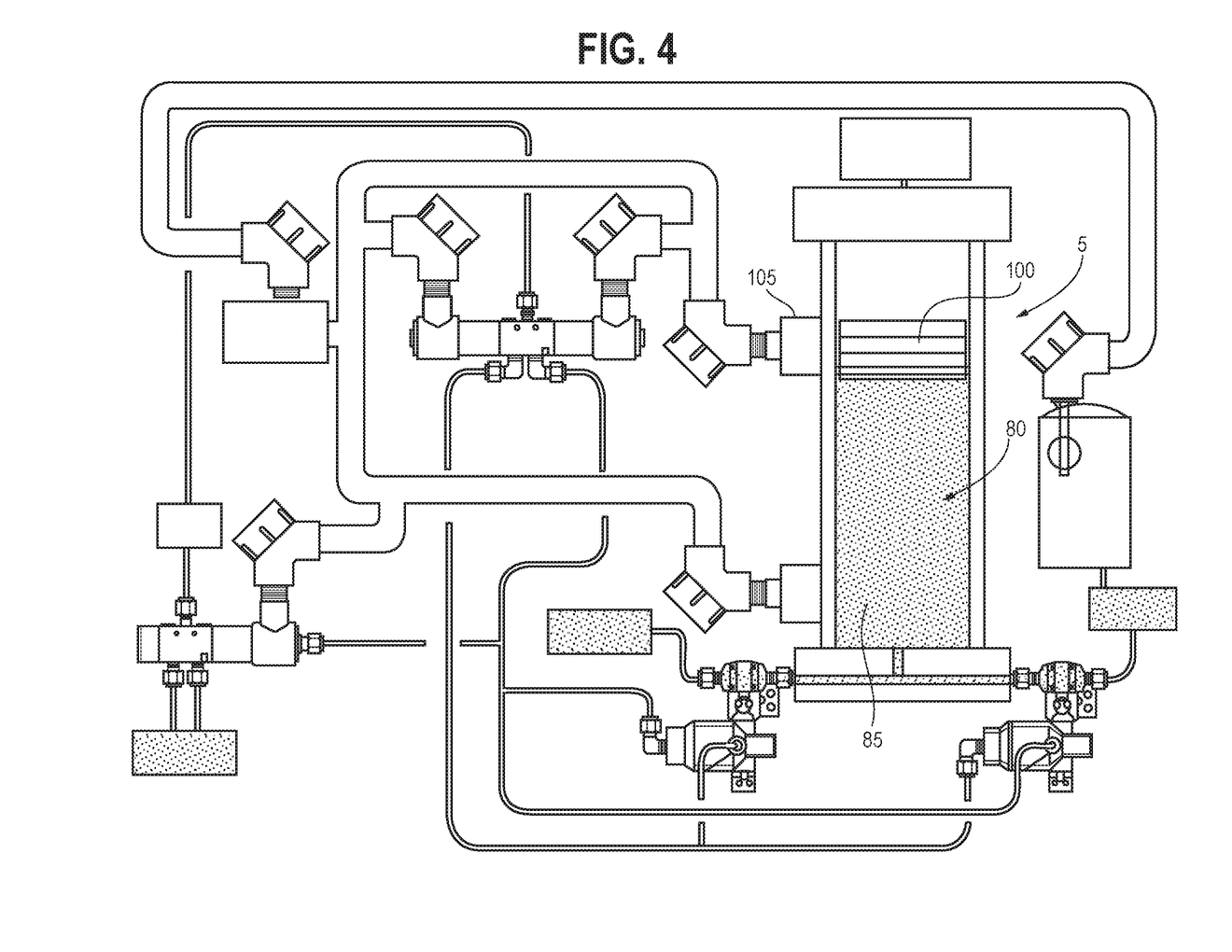
FIG. 4 is a fourth schematic of the pressure reducing system of FIGS. 1-3.

Turning to FIGS. 2 and 3, as more of the sample 85 is provided to the cylinder 5 and the first cavity 80, the piston 100 translates upwardly from the force of the high-pressure sample 85. During this time, the cylinder 5 may be monitored off-site, if so desired. The cylinder 5 continues to fill with the sample 85, preferably proportionally to flow actuations, until it reaches a level of a maximum proximity switch 105, as illustrated in FIG. 4. The level at which the proximity switch 105 may be reached may vary in various embodiments, but in a preferred embodiment, the switch 105 may be triggered when the cylinder 5 is 80% full.

Figure 5:
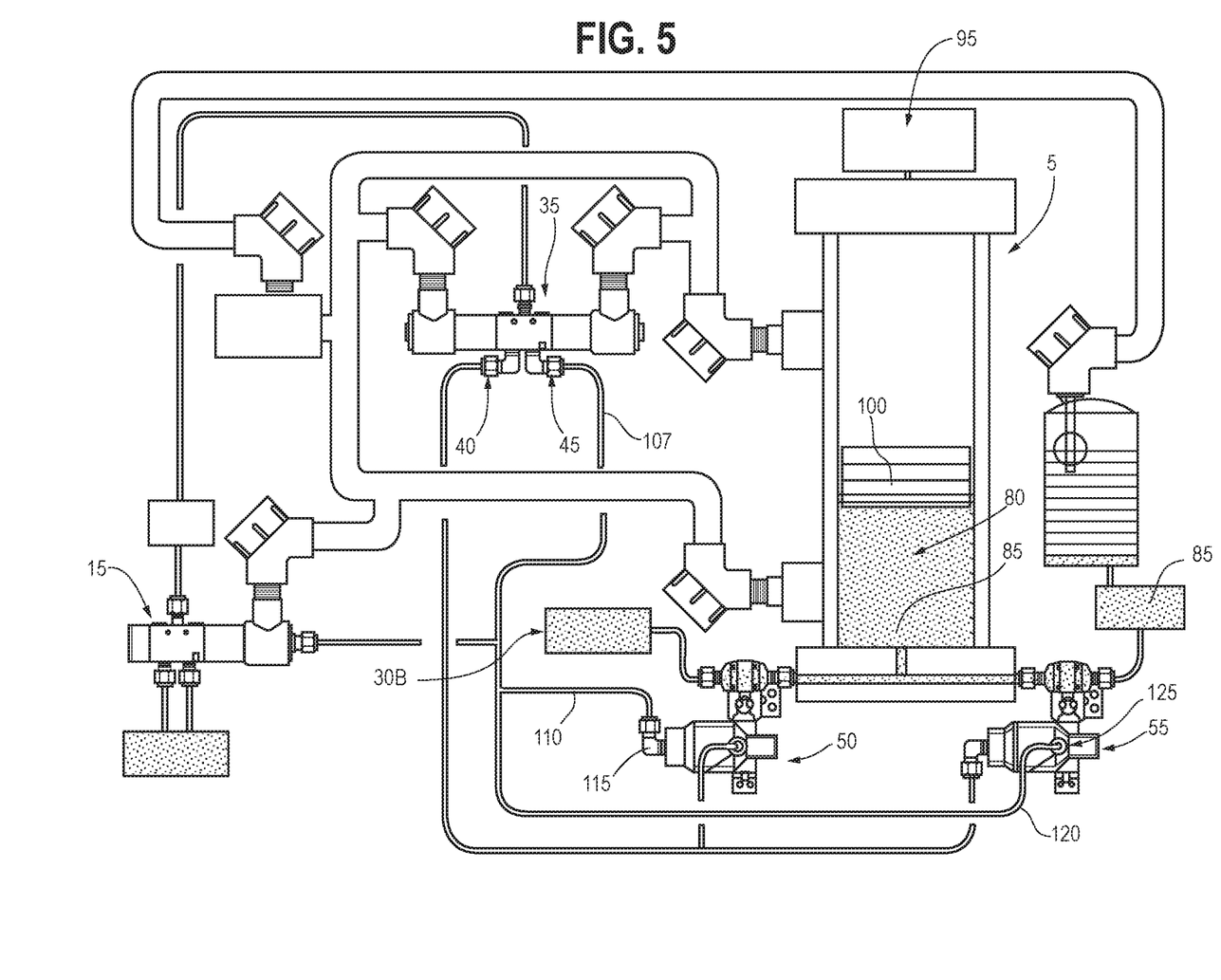
FIG. 5 is a fifth schematic of the pressure reducing system of FIGS. 1-4.

Turning to FIG. 5, after the the maximum proximity switch 105 is triggered (as illustrated in FIG. 4), the system 1 is reversed. More particularly, the dual coil four-way solenoid 35 is instructed to open the second valve 45 and close the first valve 40. Air may thus travel along a second line 107 until it encounters the valves 50, 55. A third input line 110 enters the first valve 50 at an output 115, and a fourth input line 120 enters the second valve 55 at an input 125. As such, when the solenoid 35 has caused the valve 45 to open, sample 85 moves from the cavity 80 in the cylinder 5 through the second valve 55 but is prevented from entering the first valve 50 from the sampler 30B.

With the first valve 50 closed, the backpressure applied to the piston 100 via the blanket gas applied by the tank 95 causes the sample 85 to be forced from the cylinder 5 to the sample container 10 via the valve 55. At the same time (or very near to the same time), the sample pump solenoid valve 15 stops because actuation gas pressure has been temporarily interrupted at the sample pump four-way solenoid valve 15. During this time, pipeline pressure itself does not need to be altered with, and thus the need to halting the high-pressure operation of a sampling system is not necessary.

Figure 6:
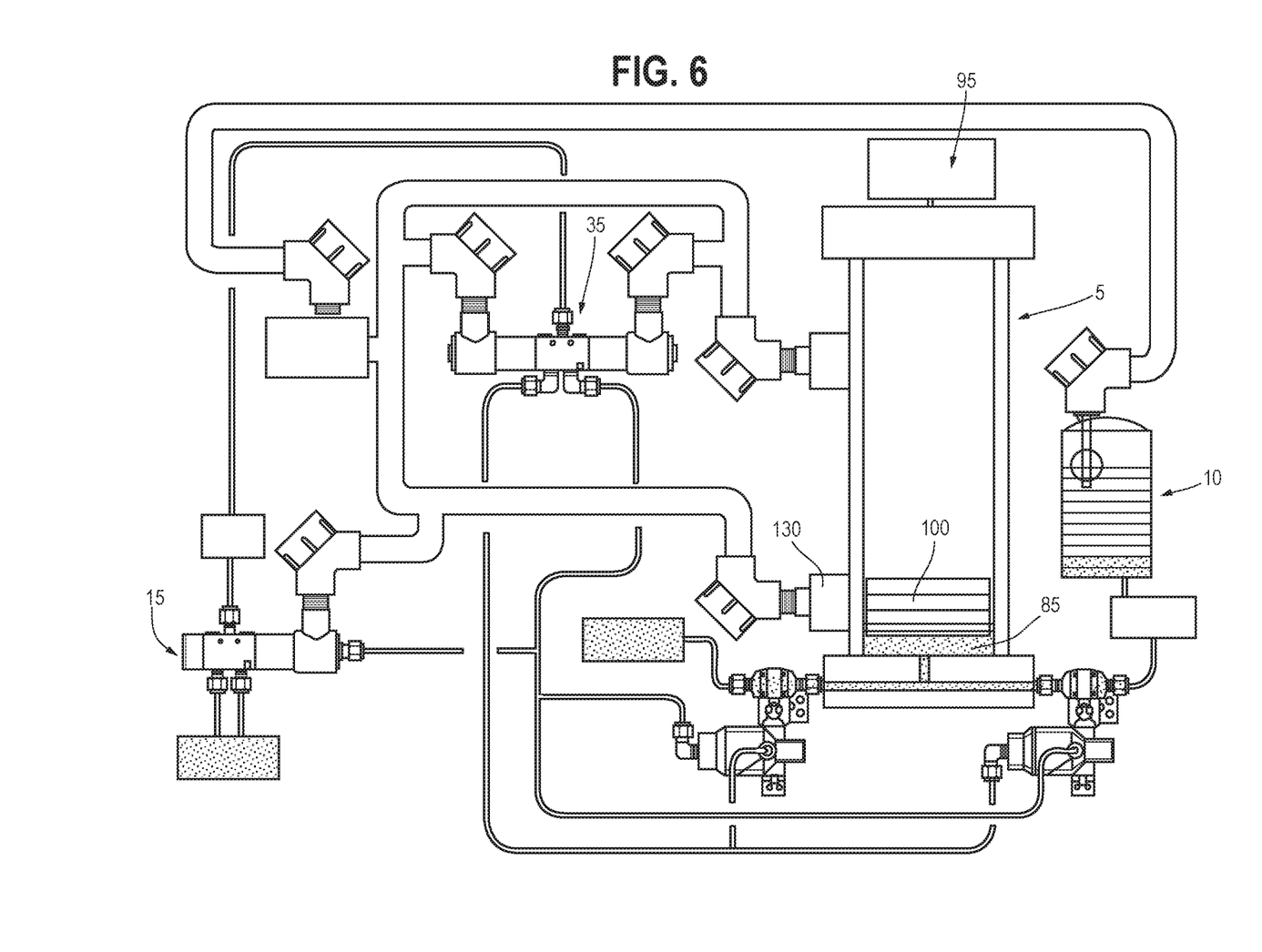
FIG. 6 is a sixth schematic of the pressure reducing system of FIGS. 1-5.

As the sample 85 is pushed out of the dual cavity cylinder 5 to the low-pressure container 10 by the pressure from the pre-charge gas tank 95, the piston 100 lowers until it contacts a minimum proximity switch 130 (illustrated in FIG. 6). The minimum proximity switch 130 energizes the dual coil solenoid four-way valve 35 and the sample pump four-way solenoid valve 15 to repeat the above-described fill cycle.

Figure 7:
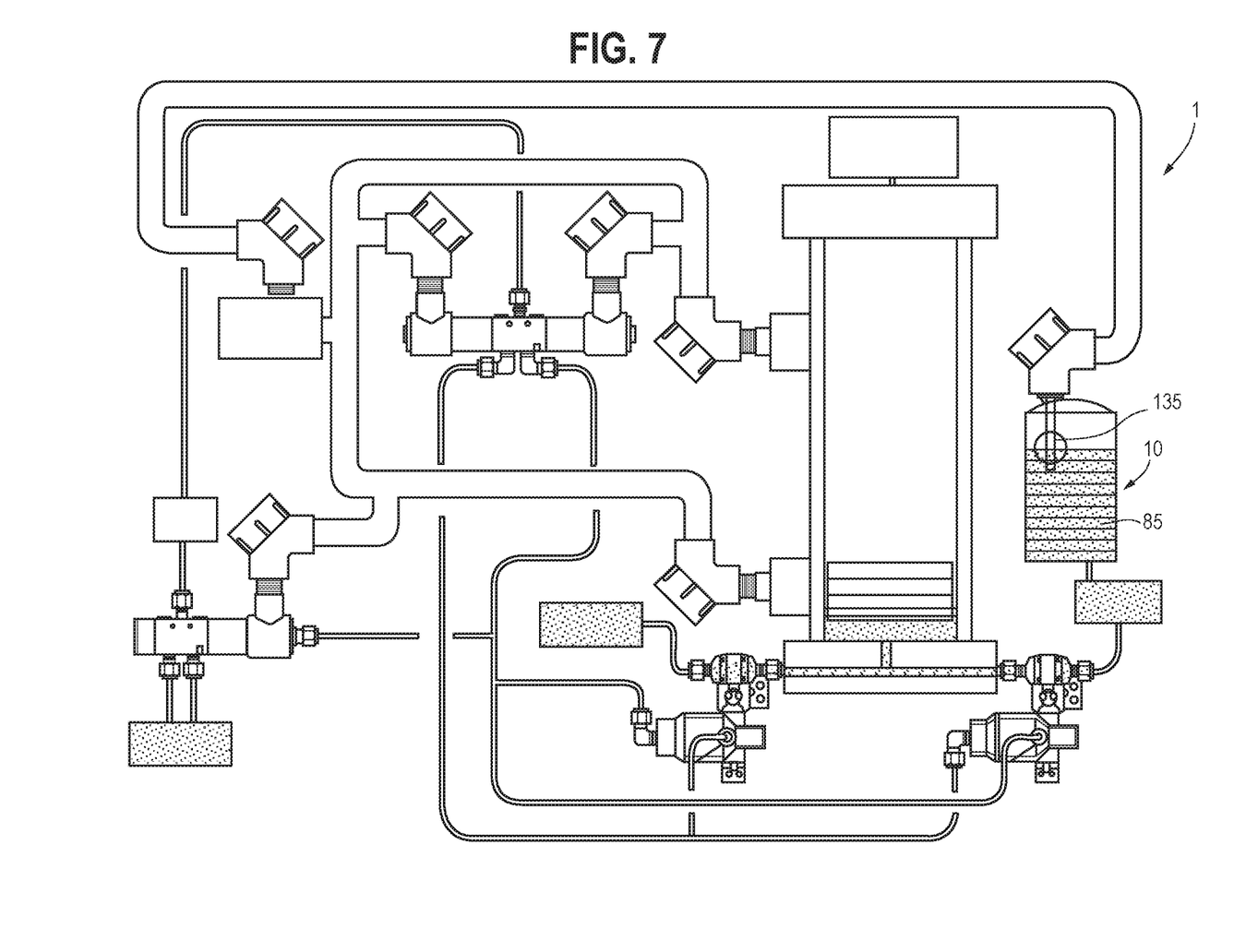
FIG. 7 is a seventh schematic of the pressure reducing system of FIGS. 1-6

The system 1 may continue to repeat the above-described cycle until the volume of sample 85 the low-pressure sample container 10 reaches 80% full (or some other predetermined maximum volume) as illustrated in FIG. 7. When it reaches such a maximum, as measured by a ball float 135 and associated high-level switch (not illustrated), or another volume measurement device known or foreseeable in the art measures the same, power to the system 1 is turned off, and operation is halted until the system 1 is reset.

In at least one alternative embodiment, the system 1 may be designed with multiple stacked relief valves operating in a sequential format to assist in pressure reduction prior to entering the dual cavity cylinder 5. For example, by stacking relief valves at a 500 psi pressure differential, the pressure cut is reduced to 500 psi at multiple stages, rather than a single 3500 psi pressure cut that takes place all at once. This can be integrated into the system 1 to use a combined methodology of sample pressure reduction, or it can conceivably be used alone.

Whether by a stacked pressure cut or by sampling against a back pressure that reduces the impact of a high pressure cut (or integrating both), sampling equipment life is extended because less strain is placed on it when a sample is taken. The function of high-pressure sampling is preserved, but it is also improved with the system 1 that takes away the negative features of previous techniques and methodologies available in the past.

As is evident from the foregoing description, certain aspects of the present invention are not limited by the particular details of the examples illustrated herein, and it is therefore contemplated that other modifications, applications, variations, or equivalents thereof, will occur to those skilled in the art. Many such changes, modifications, variations and other uses and applications of the present constructions will, however, become apparent to those skilled in the art after considering the specification and the accompanying drawings. All such changes, modifications, variations and other uses in applications which do not depart from the spirit and scope of the present inventions are deemed to be covered by the inventions which are limited only by the claims which follow.

The invention claimed is:

1. A system for sampling a crude oil sample at a reduced pressure, the system comprising:
 a cylinder;
 a piston positioned inside the cylinder;
 wherein the piston divides the cylinder into a first cavity and a second cavity;
 a gas applied to the second cavity of the cylinder to create a blanket pressure in the second cavity of the cylinder;
 a first solenoid;
 wherein when the first solenoid is activated, a sample is provided to the system; and
 a second solenoid;
 wherein when the second solenoid is activated, the sample is provided to the first cavity in the cylinder.

2. The system of claim 1, wherein the system comprises a sample container from which the sample from the first cavity of the cylinder may be transferred when the first cavity of the cylinder reaches a predetermined volume of the sample.

3. The system of claim 1, wherein the system comprises a maximum proximity switch associated with the cylinder, and wherein when a volume of the sample reaches a predetermined maximum volume in the first cavity of the cylinder, the sample is transferred from the first cavity of the cylinder to a sample container.

4. The system of claim 1, wherein the system comprises a minimum proximity switch associated with the cylinder, and wherein when a volume of the sample reaches a predetermined minimum volume in the first cavity of the cylinder, the system restarts such that the sample is provided to the first cavity of the cylinder.

5. The system of claim 1, wherein the system comprises a pre-charge gas tank that applies the blanket pressure to the second cavity of the cylinder.

6. The system of claim 1, wherein the system comprises an instrument regulator that upon activation provides air to the first solenoid.

7. A system for sampling a crude oil sample at a reduced pressure, the system comprising:
 a cylinder;
 a piston positioned inside the cylinder;
 wherein the piston divides the cylinder into a first cavity and a second cavity;
 a gas applied to the second cavity of the cylinder to create a blanket pressure in the second cavity of the cylinder;
 a first solenoid;
 wherein:
  when the first solenoid is activated, a sample is provided to the system;
  the system comprises a sample container from which the sample from the first cavity of the cylinder may be transferred when the first cavity of the cylinder reaches a predetermined volume of the sample;
  the system comprises each of a first actuation valve and a second actuation valve;
  each of the first actuation valve and the second actuation valve are in communication with the cylinder;
  when the first actuation valve is open, the sample is provided to the first cavity of the cylinder via the first actuation valve; and
  when the second actuation valve is open, the sample is provided from the first cavity of the cylinder to the sample container via the second actuation valve.

8. The system of claim 7, wherein the system comprises a second solenoid in communication with each of the first actuation valve and the second actuation valve.

9. The system of claim 8, wherein the cylinder comprises a minimum proximity switch and a maximum proximity switch, and wherein when the sample reaches a predetermined maximum volume to trigger the maximum proximity switch, the sample is directed from the first cavity of the cylinder to the sample container, and wherein when the sample reaches a predetermined minimum volume to trigger the minimum proximity switch in the cylinder, the system restarts such that the sample is provided to the first cavity of the cylinder.

10. A system for sampling a crude oil sample at a reduced pressure, the system comprising:
 a cylinder;
 a piston positioned inside the cylinder;
 wherein the piston divides the cylinder into a first cavity and a second cavity;
 a gas applied to the second cavity of the cylinder to create a blanket pressure in the second cavity of the cylinder;
 a first solenoid;
 a second solenoid;
 a first air actuated ball valve and a second air actuated ball valve, each in communication with the second solenoid;
 a sample container in communication with the cylinder via the second air actuated ball valve;
 wherein when the first solenoid is activated, the second solenoid is activated to open the first air actuated ball valve; and
 wherein when the first air actuated ball valve is open, sample is provided to the first cavity of the cylinder.

11. The system of claim 10, wherein the cylinder comprises a minimum proximity switch and a maximum proximity switch.

12. The system of claim 11, wherein when the minimum proximity switch is triggered, the first air actuated ball valve is opened.

13. The system of claim 11, wherein when the maximum proximity switch is triggered, the second air actuated ball valve is opened.

14. The system of claim 10, wherein the system comprises a pre-charge gas tank that applies the blanket pressure to the second cavity of the cylinder.

15. The system of claim 10, wherein the system comprises one or more stacked relief valves that reduce the sample pressure before it reaches the cylinder.

* * * * *